United States Patent [19]
Chang et al.

[11] Patent Number: 6,090,870
[45] Date of Patent: Jul. 18, 2000

[54] EPOXY RESIN COMPOSITION

[75] Inventors: Hsiu-Rong Chang, Taipei; Yeong-Tsyr Hwang, Hsinchu; Meng-Song Yin, Hsinchu; Kung-Lung Cheng, Hsinchu, all of Taiwan

[73] Assignee: Industrial Technology Research Institute, Hsinchu, Taiwan

[21] Appl. No.: 09/183,856

[22] Filed: Oct. 30, 1998

Related U.S. Application Data

[63] Continuation-in-part of application No. 08/841,728, Apr. 29, 1997, Pat. No. 5,844,062.
[51] Int. Cl.$^7$ ..................................................... C08L 63/00
[52] U.S. Cl. ........................... 523/443; 523/466; 525/481; 525/482; 525/484; 528/97; 528/98; 528/103
[58] Field of Search ..................................... 523/443, 466; 525/481, 482, 484; 528/97, 98, 103

[56] References Cited

U.S. PATENT DOCUMENTS 5,567,749  10/1996  Sawamura et al. ..................... 523/443

Primary Examiner—Frederick Krass
Attorney, Agent, or Firm—W. Wayne Liauh

[57] ABSTRACT

The present invention provides an epoxy resin composition, comprising:

(A) a phenol epoxy resin represented by the following formula (I)

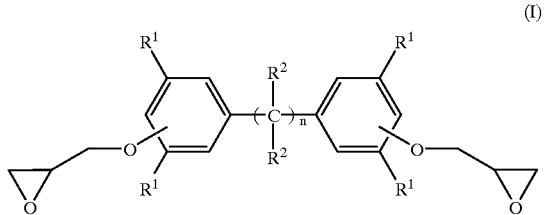

(I)

wherein
each $R^1$ is the same or different and is independently selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups,
each $R^2$ is the same or different and is independently selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups,

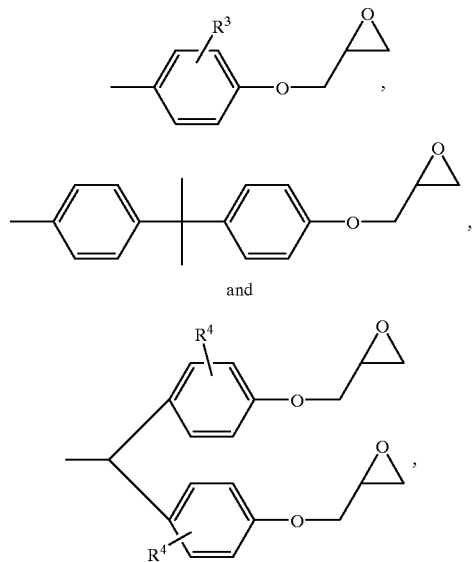

wherein $R^3$ is selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups, each $R^4$ is the same or different and is independently selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups,
n is an integer of 0 or 1;
(B) an epoxy resin different from formula (I); and
(C) a curing agent.

38 Claims, No Drawings

EPOXY RESIN COMPOSITION

This is a continuation-in-part application of U.S. patent application Ser. No. 08/841,728, filed Apr. 29, 1997, now pending.

BACKGROUND OF THE INVENTION

1. Field of the Invention

The present invention relates to an epoxy resin composition, and more particularly to an epoxy resin composition including a specific phenol epoxy resin.

2. Description of the Prior Art

During process of packaging semiconductor devices with encapsulating materials, IC chips are easily cracked as a result of the vaporization of moisture contained in the encapsulating material or internal stress. Thus, the reliability of the product is decreased.

To solve the cracking problem, various related patents have been published to provide better encapsulating materials. Shin-Etsu Chemical Company in U.S. Pat. No. 5,358,980 uses an epoxy resin containing naphthalene to increase the heat resistance (or glass transition temperature) of the encapsulating material. However, the molding fluidity of the epoxy resin composition is inferior.

Sumitomo Chemical Company in European Patent No. 700947 and Sumitomo-Bakelite Company in Japanese Application Kokai No. 8-20631 use epoxy resins with low viscosities. Thus, the amount of fillers added to the encapsulating materials can be higher. In this way, the water uptake of the resulting epoxy resin compositions can be lowered. However, the molding fluidities of the epoxy resin compositions are also lowered.

SUMMARY OF THE INVENTION

Therefore, the object of the present invention is to solve the above-mentioned problems and to provide a novel epoxy resin composition. When the epoxy resin composition is employed as the encapsulating material for semiconductor devices, the water resistance is improved, while heat resistance and fluidity are maintained or increased. Another possible outcome is for the epoxy resin composition to have a reduced coefficient of thermal expansion to improve the dimensional stability and crack resistance.

To achieve the above object, the epoxy resin composition of the present invention includes:

(A) a phenol epoxy resin represented by the following formula (I)

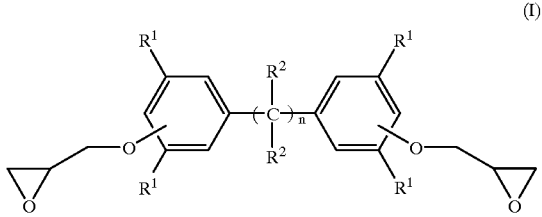

(I)

wherein
each $R^1$ is the same or different and is independently selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups, each $R^2$ is the same or different and is independently selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups,

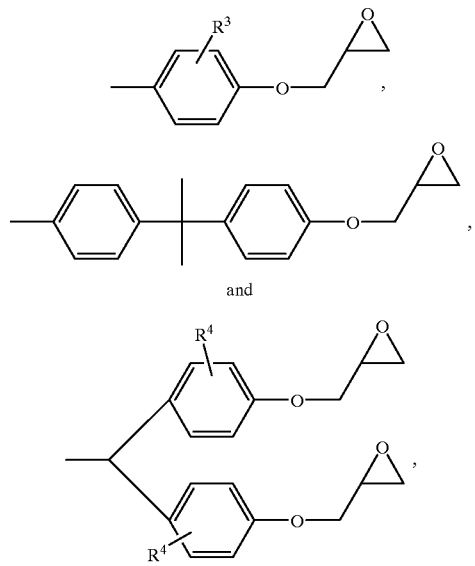

and wherein $R^3$ is selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups, and each $R^4$ is the same or different and is independently selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups, n is an integer of 0 or 1;

(B) an epoxy resin different from formula (I); and (C) a curing agent, wherein the phenol epoxy resin (A) is present in an amount of 1 to 99 wt % based on the total weight of the epoxy resins, the epoxy resin (B) is present in an amount of 1 to 99 wt % based on the total weight of the epoxy resins, and the curing agent is present in an amount of 1 to 90 wt % based on the total weight of the epoxy resin composition.

DETAILED DESCRIPTION OF THE INVENTION

According to the present invention, the epoxy resin composition includes a specific phenol epoxy resin represented by formula (I), a different epoxy resin, and a curing agent.

Each $R^1$ in formula (I) may be the same or different and is independently selected from the group consisting of hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, and $C_1$ to $C_6$ alkyl-, $C_1$ to $C_6$ cycloalkyl-, $C_1$ to $C_6$ alkenyl-, or $C_1$ to $C_6$ alkynyl-substituted phenyl or naphthyl. Representative examples of $R^1$ include hydrogen, methyl, ethyl, n-propyl, iso-propyl, n-butyl, iso-butyl, tert-butyl, n-pentyl, iso-pentyl, neo-pentyl, hexyl, phenyl, tolyl, ethylphenyl, and naphthyl. Preferred examples include hydrogen, methyl, ethyl, n-propyl, iso-propyl, n-butyl, iso-butyl, tert-butyl, pentyl, hexyl, and phenyl. Most preferred $R^1$ is hydrogen, methyl, tert-butyl, or phenyl.

Each $R^2$ is the same or different and is independently selected from the group consisting of hydrogen, $C_1$ to $C6$ alkyl, $C_1$ to $C_6$ cycloalkyl, $C_2$ to $C_6$ alkenyl, $C_2$ to $C_6$ alkynyl, phenyl, naphthyl, and $C_1$ to $C_6$ alkyl-, $C_1$ to $C_6$ cycloalkyl-, $C_2$ to $C_6$ alkenyl-, or $C_2$ to $C_6$ alkynyl-substituted phenyl or naphthyl,

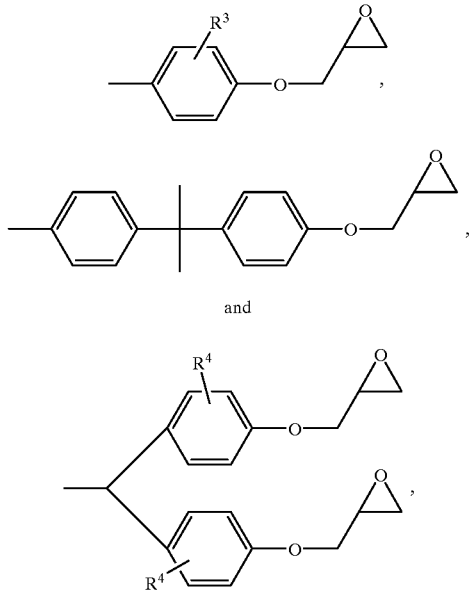

and

Representative examples of $R^2$ include hydrogen, methyl, ethyl, n-propyl, iso-propyl, n-butyl, iso-butyl, tert-butyl, n-pentyl, iso-pentyl, neo-pentyl, hexyl, phenyl, tolyl, ethylphenyl, and naphthyl. Preferred examples include hydrogen, methyl, ethyl, n-propyl, iso-propyl, n-butyl, iso-butyl, tert-butyl, pentyl, hexyl, and phenyl. Most preferred $R^2$ is hydrogen, methyl, ethyl, n-propyl, or iso-propyl.

When $R^2$ is

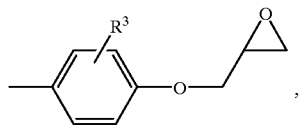

$R^3$ may be selected from the group consisting of hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, and $C_1$ to $C_6$ alkyl-, $C_1$ to $C_6$ cycloalkyl-, $C_2$ to $C_6$ alkenyl-, or $C_2$ to $C_6$ alkynyl-substituted phenyl or naphthyl. Representative examples of $R^3$ include hydrogen, methyl, ethyl, n-propyl, iso-propyl, n-butyl, iso-butyl, tert-butyl, n-pentyl, iso-pentyl, neo-pentyl, hexyl, phenyl, tolyl, ethylphenyl, and naphthyl. Preferably, $R^3$ is hydrogen, methyl, ethyl, n-propyl, iso-propyl, n-butyl, iso-butyl, tert-butyl, pentyl, hexyl, or phenyl.

When $R^2$ is

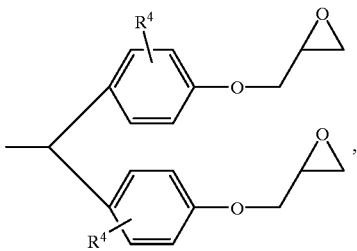

$R^4$ may be hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, $C_1$ to $C_6$ alkyl-, $C_1$ to $C_6$ cycloalkyl-, $C_1$ to $C_6$ alkenyl-, or $C_2$ to $C_6$ alkynyl-substituted phenyl or naphthyl. Representative examples of $R^4$ include hydrogen, methyl, ethyl, n-propyl, iso-propyl, n-butyl, iso-butyl, tert-butyl, n-pentyl, iso-pentyl, neo-pentyl, hexyl, phenyl, tolyl, ethylphenyl, and naphthyl. Preferably, $R^4$ is hydrogen, methyl, ethyl, n-propyl, iso-propyl, n-butyl, iso-butyl, tert-butyl, pentyl, hexyl, or phenyl, and most preferably hydrogen or phenyl.

The phenol epoxy resin (A) may be in (p, p') or (o, o') position. Representative examples of the phenol epoxy resin (A) include

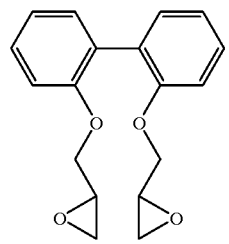

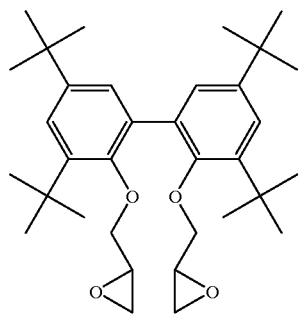

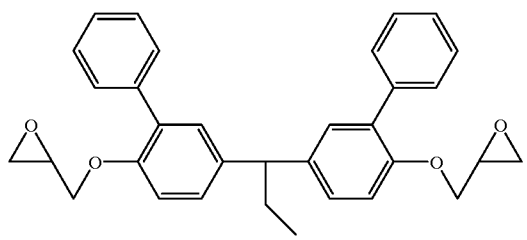

-continued

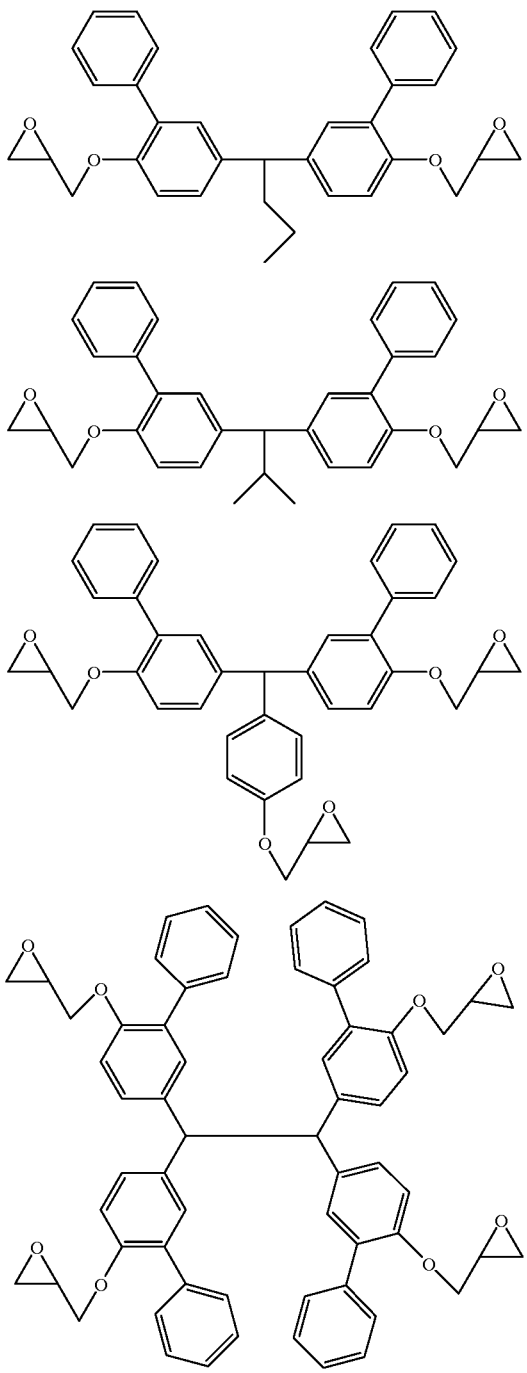

The phenol epoxy resin (A) is added in an amount of 1 to 99 wt %, preferably 1 to 95 wt %, most preferably 4 to 90 wt %, based on the total weight of the epoxy resins (A) and (B).

The epoxy resin (B), which is different from epoxy resin (A) may be a conventionally-used epoxy resin, such as phenol epoxy resins, bisphenol A epoxy resins, ortho-cresol novolak epoxy resins, and multifunctional epoxy resins. The epoxy resin (B) is added in an amount of 1 to 99 wt % based on the total weight of the epoxy resins (A) and (B).

The curing agent (C) used in the present invention may be any one conventionally used in general epoxy resins, such as amines, acid anhydrides, and phenols. The curing agent (C) is added in an amount of 1 to 90 wt % based on the weight of the total epoxy resin composition.

The amine curing agent is preferably added in an amount such that the equivalent ratio of the active hydrogen of the amine curing agent to the epoxy group of the total epoxy resins (A) and (B) is from 0.5 to 3.0. The acid anhydride curing agent is preferably added in an amount such that the equivalent ratio of the acid anhydride group of the acid anhydride curing agent to the epoxy group of the total epoxy resins (A) and (B) is from 0.5 to 3.0. The phenol curing agent is preferably added in an amount such that the equivalent ratio of the hydroxyl group of the phenol curing agent to the epoxy group of the total epoxy resins (A) and (B) is from 0.5 to 2.0, preferably from 0.6 to 1.3. Representative examples of the phenol curing agent include novolak, cresol novolak, resorcinol novolak, and bisphenol A novolak.

The epoxy resin composition of the present invention can further include a curing accelerator. The curing accelerator can be a general catalyst added in an amount of 0.1 to 20 wt %, based on the total weight of the epoxy resins (A) and (B). Representative examples of the curing accelerators include phosphorus compounds, such as triphenyl phosphine, tri(2,6-dimethoxyphenyl)phosphine, tri(para-tolyl)-phosphine, and triphenyl phosphite; imidazoles, such as 2-methyl imidazole, 2-phenyl imidazole, 2-undecyl imidazole, 2-heptadecyl imidazole, and 2-ethyl-4-methyl imidazole; tertiary amines, such as 2-dimethylaminomethylphenol, and benzyldimethylamine; and organic salts, such as 2,5-azobiscyclo[4,3,0]-5-nonene, 1,4-azobiscyclo[2,2,2]octane, and 1,8-azobiscyclo[5,4,0]-7-undecene.

The epoxy resin composition can further include additives according to practical need, such as fillers, surface treating agents, flame retardants, mold release agents, coloring agents, stress relieving agents, and mixtures thereof.

Representative examples of fillers include crystalline silica powders, fused silica powders, quartz glass powders, talc powders, aluminum silicate powders, zirconium silicate powders, aluminum powders, calcium carbonate powders, and preferably silica powders. A filler may be added in an amount of 1–97 wt %, preferably 60–90 wt %, based on the total weight of the epoxy resin composition.

A representative example of a surface treating agent is a silane coupling agent. Representative examples of flame retardants include antimony trioxide, phosphoric acid salts, and bromides. The mold releasing agent may be various waxes. The coloring agent may be carbon black. Stress relieving agents may include silicone resin or rubber.

The present invention will now be described more specifically with reference to the following examples. It is to be noted that the following examples, including the preferred embodiment of this invention, are presented herein for purposes of illustration and description, and are not intended to be exhaustive or to limit the invention to the precise form disclosed.

PREPARATIVE EXAMPLE 1

Preparation of 2,2'-bis(glycidyloxy)biphenyl (Epoxy Resin 0)

48.4 g (0.20 mol) of 3,3'5,5'-tetramethylbiphenyl-4,4'-dihydroxylbiphenyl, 0.68 g (0.01 mol) of imidazole, and 185.2 g (2.0 mol) of epichlorohydrin were placed into a 500-ml reactor equipped with a mechanical stirrer and a condensing tube. The reactor was heated to 115° C. and the reactants were allowed to react under a reflux for two hours dihydroxylbiphenyl was completely reacted (as indicated by column chromatography). The reaction products were cooled to room temperature, and the excess epichlorohydrin was removed by a rotary evaporator.

200 ml of toluene and 50 ml of 1 N sodium hydroxide solution were added to the reaction product obtained above. The mixture was heated to 90° C., stirred and reacted under a reflux for 2 hours. After being cooled down to room temperature, the organic layer and the aqueous layer were separated via an extraction procedure. The organic content in the aqueous layer was further extracted using toluene (160 ml, twice). The organic layers were then combined, dried with sodium sulfate anhydrite, filtered, and rotary-evaporated to obtain a raw product.

The raw product was purified by silica gel chromatography to obtain a colorless liquid. The yield was 92%.

The NMR data of the final product are as follows:

$^1$H NMR (CDCl$_3$, 200 MHz) δ 2.54 (2H, dd, J=5.1, 2.5 Hz), 2.70 (2H, dd, J=5.1, 4.0 Hz), 3.16 (2H, dddd, J=5.5, 4.0, 2.9, 2.5 Hz), 3.93 (2H, dd, J=11.2, 5.5 Hz), 4.17 (2H, dd, J=11.2, 2.9 Hz), 6.95 (2H, dd, J=8.1, <1.0 Hz), 7.03 (2H, dd, J=7.3, 1.0 Hz), 7.24 (4H, m). $^{13}$C NMR (CDCl$_3$, 100 MHz) δ 44.3 (t), 50.2 (d), 68.9 (t), 112.6 (d), 121.0 (d), 128.3 (s), 128.5 (d), 131.4 (d), 155.9 (s).

PREPARATIVE EXAMPLE 2

Preparation of 2-2'-bis(4-glycidyloxy)-3,3',5,5'-tetra-tert-butylbiphenyl (Epoxy Resin D)

The procedures were the same as described in Preparative Example 1, except that during the purification step, the reaction product was crystallized using ethanol to obtain a white solid product. The reaction yield was 85%. The melting point was 185–186° C.

The spectroscopic data of the product are as follows:

$^1$H NMR (CDCl$_3$, 200 MHz) δ 1.33 (18H, s), 1.43 (18H, s), 2.19 (2H, dd, J=4.9, 2.7 Hz), 2.63 (2H, dd, J=4.9, 4.4 Hz), 3.00 (2H, dddd, J=5.5, 4.4, 3.3, 2.7 Hz), 3.57 (2H, dd, J=11.0, 5.6 Hz), 3.68 (2H, dd, J=11.0, 3.3 Hz), 7.14 (2H, d, J=2.4 Hz), 7.38 (2H, d, J=2.4 Hz) MS (m/e): 522 (M$^+$), 466 (base), 451, 337, 225, 57, 41, 29.

PREPARATIVE EXAMPLE 3

Preparation of 1,1'-bis[(4-glycidyloxy-3-phenyl)phenyl]-2-methylpropane (Epoxy Resin B)

The procedures were the same as described in Preparative Example 1, except that during the purification step, the reaction product was extracted with a mixture of methyl ethyl ketone and toluene (3:1) and re-crystallized in toluene to obtain a white solid product. The reaction yield was 85–90%. The melting point was 131–134° C.

The spectroscopic data of the final product are as follows:

$^1$H NMR (CDCl$_3$, 200 MHz) δ 0.83 (6H, d, J=6.5 Hz), 2.37 (1H, dsept, J=11.0, 6.5 Hz), 2.57 (2H, dd, J=4.9, 2.7 Hz), 2.71 (2H, dd, J=4.9, 4.4 Hz), 3.15 (2H, dddd, J=5.0, 4.4, 3.0, 2.7 Hz), 3.31 (1H, d, J=11.0 Hz), 3.86 (2H, dd, J=11.1, 5.0 Hz), 4.07 (2H, dd, J=11.1, 3.0 Hz), 6.81 (2H, d, J=8.2 Hz), 7.12 (2H, dd, J=8.2, 2.0 Hz), 7.20 (2H, d, J=2.0 Hz), 7.30 (6H, m), 7.45 (4H, dd, J=6.9, 1.7 Hz).

EXAMPLES 1–3 AND COMPARATIVE EXAMPLE 1

Epoxy resins, curing agent, 82 wt % of fused silica powder, 0.85 wt % of a curing accelerator, and 1.75 wt % of additives (e.g., surface treating agents, flame retardants, mold release agents, and coloring agents) were mixed thoroughly with a two-roll mill at 80–130° C. The mixture was then crushed into powders for analysis.

The formulae and epoxy equivalents of the epoxy resins used are shown in Table 1. The amounts of the epoxy resins and curing agent added are shown in Table 2. Epoxy resin Y is conventional, and epoxy resins B, D, and O are the specific phenol epoxy resins of the present invention, which were prepared from Preparative Examples 1–3 respectively. The curing agent used was phenol-formaldehyde novolak resin, which has a softening point of 70–75° C. and a hydroxy equivalent of 103 g/eq.

The powders of the epoxy resin compositions were evaluated by the following analysis methods:

(A) Water uptake

The sample powders (the powders of the epoxy resin compositions) were molded according to SEMI G66-96 to form test pieces with a thickness of 3 mm and a diameter of 50 mm. After being postcured at 175° C., the test pieces were put into a constant temperature humidity chamber, which was set at a temperature of 85° C. and a relative humidity of 85%, for 72 hours. A variation in weight was measured before and after the chamber to calculate the water uptake.

(B) Gel time

The sample powders were placed on a cure plate at 175° C., and stirred continuously until the sample powders lost fluidity.

(C) Spiral flow length

The testing was conducted according to SEMI G11-88. The main conditions were as follows: the curing time in the mold was 90 seconds, the molding temperature was 175° C., the transfer pressure was 6.895±0.177 MPa (1000±25 psi), and the transfer speed was at least 25.4 mm/sec (1'/sec).

(D) Glass transition temperature (Tg) and coefficient of thermal expansion

The testing was conducted according to SEMI G13-88. The test pieces were prepared with a hot press by molding the sample powders into a cylindrical shape with a diameter of 5 mm, and then post cured at 175° C. for over 6 hours. The test pieces were sliced into 5 mm thick disks and analyzed using a thermomechanical analyzer at a heating rate of 5° C./min.

From the results shown in Table 2, it is seen that the composition containing epoxy resin B or D has a lower water uptake and coefficient of thermal expansion, and an increased glass transition temperature. Further, the composition containing epoxy resin D or O has better fluidity.

EXAMPLES 4–6 AND COMPARATIVE EXAMPLES 2 AND 3

The same procedures as described in Example 1 were employed, except that the amounts of the components in the epoxy resin compositions were varied. The components and properties of the compositions are summarized in Table 3.

Epoxy resin M is a multifunctional epoxy resin available from Nippon Kayaku Company under the trade name EPPN-501, which has an epoxy equivalent of 160–170. Epoxy resin N is an o-cresol novolac epoxy resin with an epoxy equivalent of 190–205, available from Sumitomo Chemical Company under the trade name ESCN-195XF.

From the results shown in Table 3, it can be seen that a composition containing epoxy resin O or B has a lower water uptake and better fluidity compared with a conventional one.

From the results of the above examples, it can be seen that the epoxy resin composition of the present invention has low water uptake, a low coefficient of thermal expansion, high fluidity, and improved heat resistance. Therefore, the epoxy resin composition of the present invention is particularly suitable for use as an encapsulating material for encapsulating semiconductors. Also, it can be used as a molding material, powder coating material, printed circuit board material, and an adhesive.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application, thereby enabling those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

TABLE 2

| | Example | Ex. 1 | Ex. 2 | Ex. 3 | Comp. Ex. 1 |
|---|---|---|---|---|---|
| Composition (wt %) | Epoxy Resin Y | 8.66 | 9.65 | 10.20 | 10.62 |
| | Epoxy Resin B | 2.16 | — | — | — |
| | Epoxy Resin D | — | 1.07 | — | — |
| | Epoxy Resin O | — | — | 0.42 | — |
| | Curing agent | 4.58 | 4.68 | 4.78 | 4.78 |
| Properties | Gel time (sec.) | 27 | 29 | 28 | 28 |
| | Spiral flow length (in) | 40 | 49 | 59 | 40 |
| | Water uptake (wt.%) @85° C./85%RH/72h | 0.192 | 0.193 | 0.211 | 0.199 |
| | Tg (° C.) | 150 | 159 | 138 | 148 |
| | Coeff. of thermal expansion (ppm/° C.) | | | | |
| | <Tg | 11 | 10 | 13 | 13 |
| | >Tg | 37 | 37 | 47 | 45 |

TABLE 1

| | Formula | Epoxy Equivalent (g/eq) |
|---|---|---|
| Yuka Shell Co. YX-4000H (Epoxy Resin Y) | | 192 |
| 2,2'-bis(glycidyloxy) biphenyl (Epoxy Resin O) | | 177 |
| 2,2'-bis(glycidyloxy)-3,3',5,5'-tetra-tert-butyl biphenyl (Epoxy Resin D) | | 261 |
| 1,1'-bis[(4-glycidyloxy-3 phenyl)phenyl]-2-methyl propane (Epoxy B) | R = i-Pr (isopropyl) | 253 |

TABLE 3

| Example | | Ex. 4 | Ex. 5 | Comp. Ex. 2 | Ex. 6 | Comp. Ex. 3 |
|---|---|---|---|---|---|---|
| Composition (wt %) | Epoxy Resin O | 2.06 | — | — | 5.24 | — |
| | Epoxy Resin M | 8.24 | 3.55 | 10.3 | — | — |
| | Epoxy Resin N | — | — | — | 5.24 | 10.48 |
| | Epoxy Resin B | — | 10.62 | — | — | — |
| | Curing agent | 5.25 | 5.38 | 5.25 | 5.07 | 5.07 |
| | Filler | 82 | 78 | 82 | 82 | 82 |
| | Curing accelerator | 0.7 | 0.7 | 0.7 | 0.7 | 0.7 |
| | Additives | 1.75 | 1.75 | 1.75 | 1.75 | 1.75 |
| Properties | Gel time (sec.) | 20 | 30 | 17 | 22 | 15 |
| | Spiral flow length (in) | 29 | 46 | 21 | 31 | 12 |
| | Water uptake (wt. %) @85° C./85%RH/72h | 0.291 | 0.259 | 0.306 | 0.232 | 0.234 |
| | Tg (° C.) | 161 | 150 | — | 147 | — |
| | Coeff. of thermal expansion (ppm/° C.) | | | | | |
| | <Tg | 12 | 15 | — | 13 | — |
| | >Tg | 45 | 57 | — | 42 | — |

What is claimed is:

1. An epoxy resin composition, comprising:

(A) a phenol epoxy resin represented by the following formula (I)

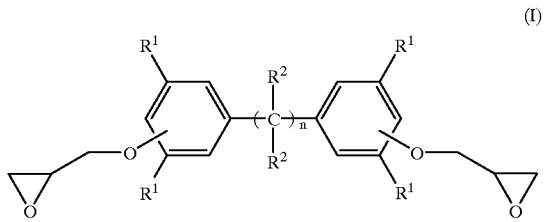

wherein each $R^1$ is the same or different and is independently selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups, each $R^2$ is the same or different and is independently selected from the group consisting of hydrogen, $C_1$ to $C_6$ hydrocarbyl groups, $C_6$ to $C_{10}$ aromatic groups, $C_1$ to $C_6$ hydrocarbyl-substituted $C_6$ to $C_{10}$ aromatic groups,

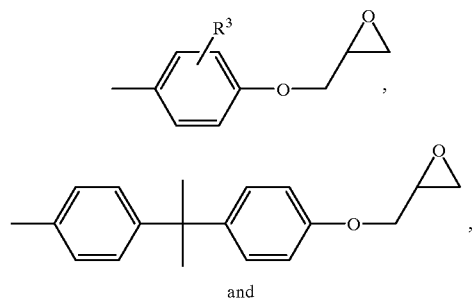

and

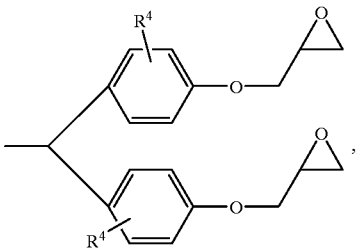

wherein $R^3$ is selected from the group consisting of hydrogen, $C_1$ to $C_{10}$ hydrocarbyl groups, $C_6$ to $C_{10}$ aromatic groups, and $C_1$ to $C_6$ hydrocarbyl-substituted $C_6$ to $C_{10}$ aromatic groups, and each $R^4$ is the same or different and is independently selected from the group consisting of hydrogen, $C_1$ to $C_6$ hydrocarbyl groups, $C_6$ to $C_{10}$ aromatic groups, and $C_1$ to $C_6$ hydrocarbyl-substituted $C_6$ to $C_{10}$ aromatic groups, n is an integer of 0 or 1;

(B) an epoxy resin different from formula (I); and (C) a curing agent, wherein the phenol epoxy resin (A) is present in an amount of 1 to 99 wt % based on the total weight of the epoxy resins, the epoxy resin (B) is present in an amount of 1 to 99 wt % based on the total weight of the epoxy resins, and the curing agent is present in an amount of 1 to 90 wt % based on the total weight of the epoxy resin composition; wherein, said phenol epoxy resin is an ortho-biphenyl epoxy resin.

2. The epoxy resin composition as claimed in claim 1, wherein each $R^1$ is independently selected from the group consisting of hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, and $C_1$ to $C_6$ alkyl-, $C_1$ to $C_6$ cycloalkyl-, $C_2$ to $C_6$ alkenyl-, or $C_2$ to $C_6$ alkynyl-substituted phenyl or naphthyl.

3. The epoxy resin composition as claimed in claim 1, wherein each $R^1$ is independently selected from the group consisting of hydrogen, methyl, ethyl, n-propyl, iso-propyl, n-butyl, iso-butyl, tert-butyl, n-pentyl, iso-pentyl, neo-pentyl, hexyl, phenyl, tolyl, ethylphenyl, and naphthyl.

4. The epoxy resin composition as claimed in claim 1, wherein each $R^1$ is independently selected from the group consisting of hydrogen, methyl, ethyl, n-propyl, iso-propyl, n-butyl, iso-butyl, tert-butyl, pentyl, hexyl, and phenyl.

5. The epoxy resin composition as claimed in claim 4, wherein each $R^1$ is independently selected from the group consisting of hydrogen, methyl, tert-butyl, and phenyl.

6. The epoxy resin composition as claimed in claim 1, wherein each $R^2$ is independently selected from the group consisting of hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, $C_1$ to $C_6$ alkyl-, $C_1$ to $C_6$ cycloalkyl-, $C_2$ to $C_6$ alkenyl-, or $C_2$ to $C_6$ alkynyl-substituted phenyl or naphthyl,

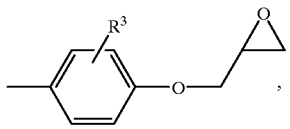

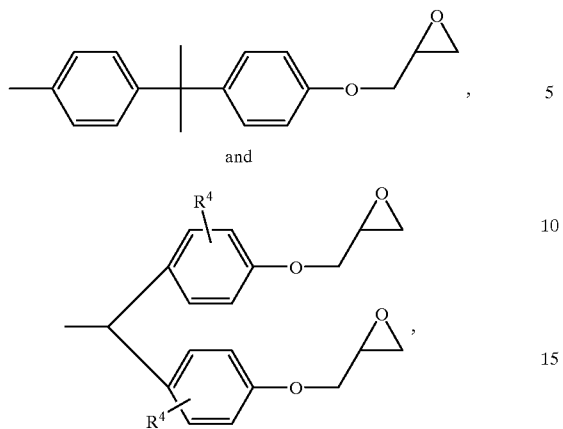

and

7. The epoxy resin composition as claimed in claim 1, wherein each $R^2$ is independently selected from the group consisting of hydrogen, methyl, ethyl, n-propyl, iso-propyl, n-butyl, iso-butyl, tert-butyl, n-pentyl, iso-pentyl, neo-pentyl, hexyl, phenyl, tolyl, ethylphenyl, and naphthyl.

8. The epoxy resin composition as claimed in claim 1, wherein each $R^2$ is independently selected from the group consisting of hydrogen, methyl, ethyl, n-propyl, iso-propyl, n-butyl, iso-butyl, tert-butyl, pentyl, hexyl, and phenyl.

9. The epoxy resin composition as claimed in claim 8, wherein each $R^2$ is independently selected from the group consisting of hydrogen, methyl, ethyl, n-propyl, and iso-propyl.

10. The epoxy resin composition as claimed in claim 1, wherein $R^3$ is selected from the group consisting of hydrogen, alkyl, $C_1$ to $C_6$ cycloalkyl, $C_2$ to $C_6$ alkenyl, $C_2$ to $C_6$ alkynyl, phenyl, naphthyl, and $C_1$ to $C_6$ alkyl-, $C_1$ to $C_6$ cycloalkyl-, $C_2$ to $C_6$ alkenyl-, or $C_2$ to $C_6$ alkynyl-substituted phenyl or naphthyl.

11. The epoxy resin composition as claimed in claim 1, wherein $R_3$ is selected from the group consisting of hydrogen, methyl, ethyl, n-propyl, iso-propyl, n-butyl, iso-butyl, tert-butyl, n-pentyl, iso-pentyl, neo-pentyl, hexyl, phenyl, tolyl, ethylphenyl, and naphthyl.

12. The epoxy resin composition as claimed in claim 1, wherein $R^3$ is selected from the group consisting of hydrogen, methyl, ethyl, n-propyl, iso-propyl, n-butyl, iso-butyl, tert-butyl, pentyl, hexyl, and phenyl.

13. The epoxy resin composition as claimed in claim 1, wherein each $R^4$ is independently selected from the group consisting of hydrogen, $C_1$ to $C_6$ alkyl, $C_1$ to $C_6$ cycloalkyl, $C_2$ to $C_6$ alkenyl, $C_2$ to $C_6$ alkynyl, phenyl, naphthyl, and $C_1$ to $C_6$ alkyl-, $C_1$ to $C_6$ cycloalkyl-, $C_2$ to $C_6$ alkenyl-, or $C_2$ to $C_6$ alkynyl-substituted phenyl or naphthyl.

14. The epoxy resin composition as claimed in claim 1, wherein each $R^4$ is independently selected from the group consisting of hydrogen, methyl, ethyl, n-propyl, iso-propyl, n-butyl, iso-butyl, tert-butyl, n-pentyl, iso-pentyl, neo-pentyl, hexyl, phenyl, tolyl, ethylphenyl, and naphthyl.

15. The epoxy resin composition as claimed in claim 1, wherein each $R^4$ is independently selected from the group consisting of hydrogen, methyl, ethyl, n-propyl, iso-propyl, n-butyl, iso-butyl, tert-butyl, pentyl, hexyl, and phenyl.

16. The epoxy resin composition as claimed in claim 15, wherein each $R^4$ is independently selected from hydrogen or phenyl.

17. The epoxy resin composition as claimed in claim 1, wherein said phenol epoxy resin (A) is selected from the group consisting of:

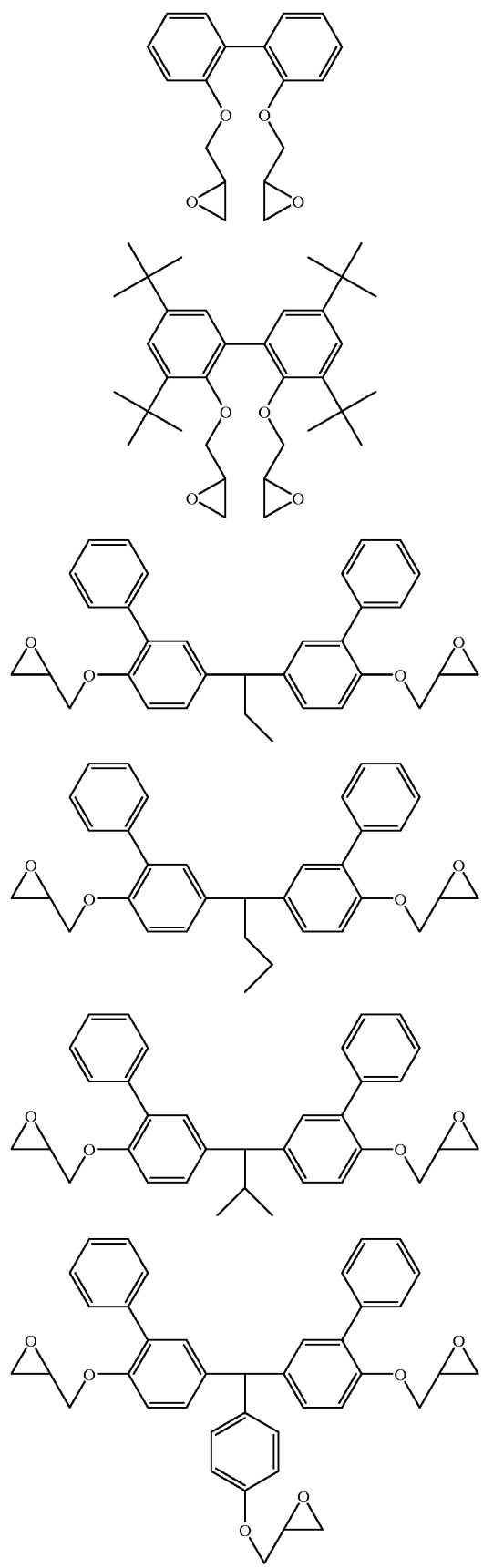

-continued and

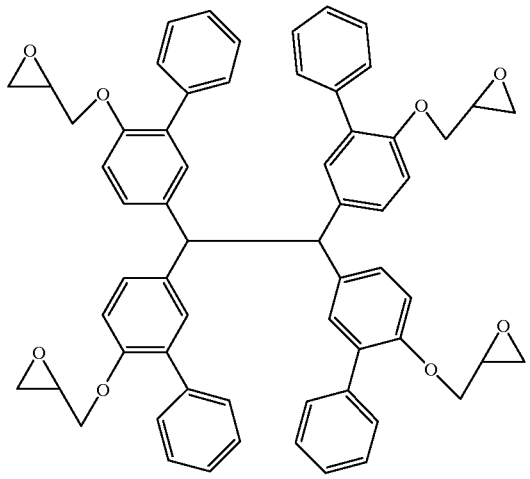

18. The epoxy resin composition as claimed in claim 1, wherein the phenol epoxy resin (A) is present in an amount of 4 to 90 wt % based on the total weight of the epoxy resins (A) and (B).

19. The epoxy resin composition as claimed in claim 1, wherein the epoxy resin (B) is selected from the group consisting of phenol epoxy resins, bisphenol A epoxy resins, ortho-cresol novolak epoxy resins, and multifunctional epoxy resins.

20. The epoxy resin composition as claimed in claim 1, wherein the curing agent (C) is selected from the group consisting of amines, acid anhydrides, and phenols.

21. The epoxy resin composition as claimed in claim 20, wherein the curing agent (C) is an amine.

22. The epoxy resin composition as claimed in claim 21, wherein the equivalent ratio of the active hydrogen of the amine curing agent to the epoxy group of the total epoxy resins (A) and (B) is from 0.5 to 3.0.

23. The epoxy resin composition as claimed in claim 20, wherein the curing agent (C) is an acid anhydride.

24. The epoxy resin composition as claimed in claim 23, wherein the equivalent ratio of the acid anhydride group of the acid anhydride curing agent to the epoxy group of the total epoxy resins (A) and (B) is from 0.5 to 3.0.

25. The epoxy resin composition as claimed in claim 20, wherein the curing agent (C) is a phenol curing agent selected from the group consisting of novolak, cresol novolak, resorcinol novolak, and bisphenol A novolak.

26. The epoxy resin composition as claimed in claim 25, wherein the equivalent ratio of the hydroxyl group of the phenol curing agent to the epoxy group of the total epoxy resins (A) and (B) is from 0.5 to 2.0.

27. The epoxy resin composition as claimed in claim 25, wherein the equivalent ratio of the hydroxyl group of the phenol curing agent to the epoxy group of the total epoxy resins (A) and (B) is from 0.6 to 1.3.

28. The epoxy resin composition as claimed in claim 1, further comprising a curing accelerator.

29. The epoxy resin composition as claimed in claim 28, wherein the curing accelerator is present in an amount of 0.1 to 20 wt %, based on the total weight of the epoxy resins (A) and (B).

30. The epoxy resin composition as claimed in claim 28, wherein the curing accelerator is selected from the group consisting of phosphorus compounds, imidazoles, tertiary amines, and organic salts.

31. The epoxy resin composition as claimed in claim 30, wherein the curing accelerator is a phosphorus compound selected from the group consisting of triphenyl phosphine, tri(2,6-dimethoxyphenyl)phosphine, tri(para-tolyl)-phosphine, and triphenyl phosphite; an imidazole selected from the group consisting of 2-methyl imidazole, 2-phenyl imidazole, 2-undecyl imidazole, 2-heptadecyl imidazole, and 2-ethyl-4-methyl imidazole; a tertiary amine selected from the group consisting of 2-dimethylaminomethylphenol and benzyldimethylamine; or an organic salt selected from the group consisting of 2,5-azobiscyclo[4,3,0]-5-nonene, 1,4-azobiscyclo[2,2,2]octane, and 1,8-azobiscyclo[5,4,0]-7-undecene.

32. The epoxy resin composition as claimed in claim 1, further comprising an additive selected from the group consisting of fillers, surface treating agents, flame retardants, mold release agents, coloring agents, stress relieving agents, and mixtures thereof.

33. The epoxy resin composition as claimed in claim 32, wherein the filler is selected from the group consisting of crystalline silica powders, fused silica powders, quartz glass powders, talc powders, aluminum silicate powders, zirconium silicate powders, aluminum powders, and calcium carbonate powders.

34. The epoxy resin composition as claimed in claim 32, wherein the filler is present in an amount of 60 to 90 wt % based on the total weight of the composition.

35. The epoxy resin composition as claimed in claim 32, wherein the surface treating agent is a silane coupling agent, and the flame retardant is selected from the group consisting of antimony trioxide, phosphoric acid salts, and bromides.

36. The epoxy resin composition as claimed in claim 1, which comprises an encapsulating material, molding material, power coating material, adhesive, or printed circuit board material.

37. The epoxy resin composition as claimed in claim 1, wherein n=1.

38. The epoxy resin composition as claimed in claim 1, wherein n=0, and said epoxy groups are in ortho-ortho positions.

* * * * *